(12) United States Patent
Khamene et al.

(10) Patent No.: US 7,869,562 B2
(45) Date of Patent: Jan. 11, 2011

(54) AUTOMATIC PATIENT POSITIONING SYSTEM

(75) Inventors: Ali Khamene, Princeton, NJ (US); Stefan Käpplinger, Jena (DE); Gabriel Haras, Mücke (DE); Eike Rietzel, Darmstadt (DE)

(73) Assignee: Siemens Aktiengesellschaft, München (DE)

( * ) Notice: Subject to any disclaimer, the term of this patent is extended or adjusted under 35 U.S.C. 154(b) by 37 days.

(21) Appl. No.: 12/406,233

(22) Filed: Mar. 18, 2009

(65) Prior Publication Data

US 2009/0285357 A1 Nov. 19, 2009

Related U.S. Application Data

(60) Provisional application No. 61/054,214, filed on May 19, 2008.

(51) Int. Cl.
*H05G 1/60* (2006.01)
*A61B 6/04* (2006.01)
*G01D 18/00* (2006.01)

(52) U.S. Cl. .................................. 378/20; 209/207

(58) Field of Classification Search ............. 378/4, 378/20, 62, 68, 205–209
See application file for complete search history.

(56) References Cited

U.S. PATENT DOCUMENTS

| | | | |
|---|---|---|---|
| 6,229,873 | B1 | 5/2001 | Bani-Hashemi |
| 7,433,503 | B2 * | 10/2008 | Cherek et al. ............ 382/128 |
| 2002/0067793 | A1 | 6/2002 | Stierstorfer |
| 2003/0133602 | A1 | 7/2003 | Bani-Hashemi |
| 2004/0081341 | A1 | 4/2004 | Cherek |
| 2004/0258210 | A1 | 12/2004 | Ritter |
| 2007/0172102 | A1 | 7/2007 | Hempel |

FOREIGN PATENT DOCUMENTS

| | | |
|---|---|---|
| WO | WO 2004089204 A1 | 10/2004 |
| WO | WO 2006071002 A1 | 7/2006 |
| WO | WO 2007111669 A2 | 10/2007 |

OTHER PUBLICATIONS

Kao, et al. "The registration of CT image to the patient head by using an automated laser surface scanning system-a phantom study" Published by Computer Methods and Programs in Biomedicine, Elsevier, vol. 83, No. 1, Jul. 1, 2006 (pp. 1-11); Magazine.
Khamene et al., "Characterization of Internal Organ Motion Using Skin Marker Positions", MICCAI (2) 2004:526-533.
Ehrhardt et al., "An Anatomical Atlas to Support the Virtual Planning of Hip Opeartions" CVPR 2007.

* cited by examiner

*Primary Examiner*—Irakli Kiknadze
(74) *Attorney, Agent, or Firm*—Donald B. Paschburg

(57) ABSTRACT

A patient positioning system for positioning a patient relative to radiographic equipment. The system includes: a 3D optical imaging system for optically scanning the patient, such 3D optical imaging system having a focal plane and providing, for each position on the object, data representative of the intensity of reflected energy received by the system from such position and data representative of distance from such position on the object to the focal plane; a table apparatus for supporting the patient and for moving the table relative to the radiographic equipment in response to positioning signals; and a processor responsive to data from the radiographic equipment and the data from the a 3D optical imaging system for producing the positioning signals. The system enables a method for displaying temporal changes in a patient positioned with a bore of radiographic equipment.

12 Claims, 4 Drawing Sheets

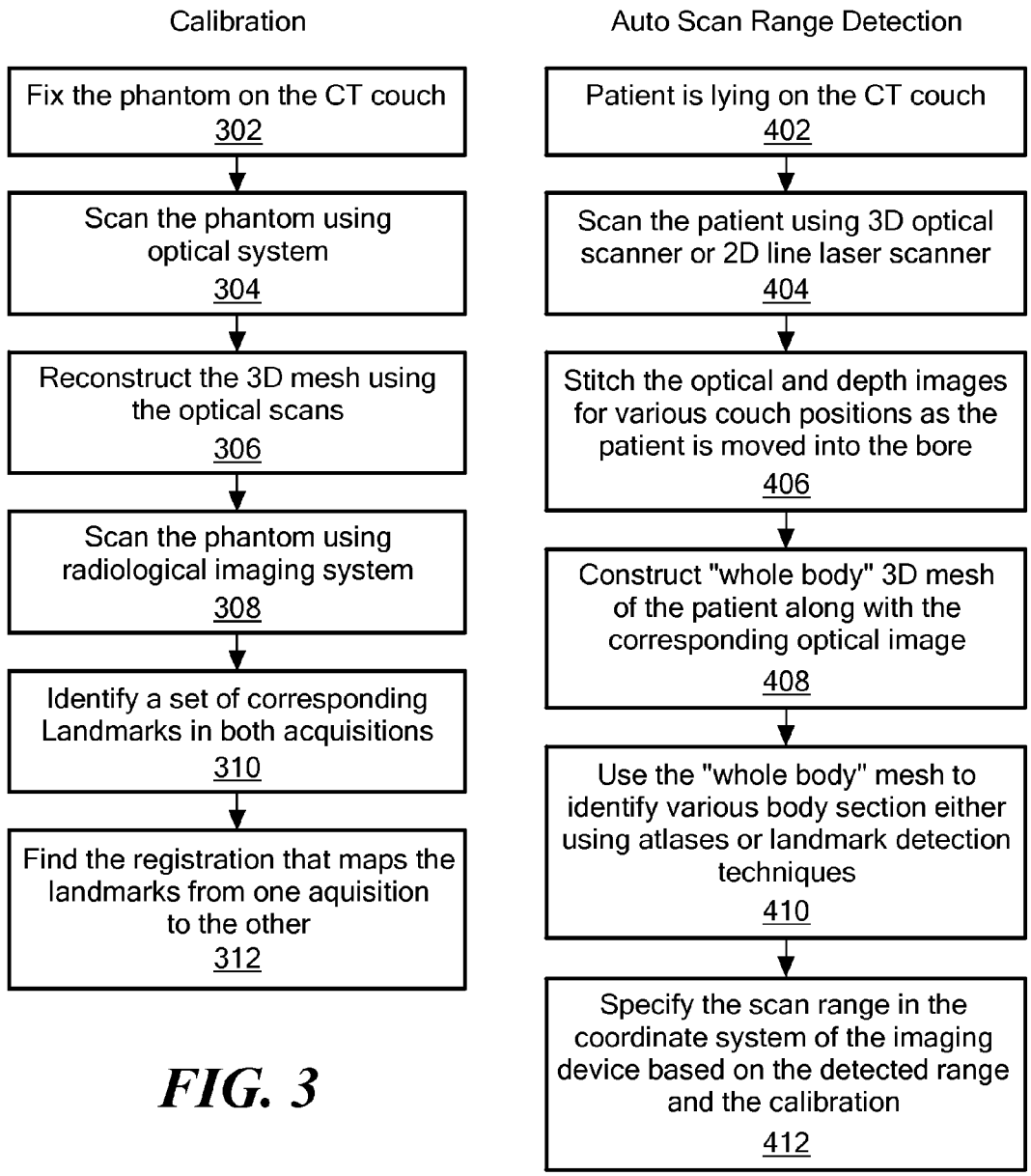

AUTOMATIC PATIENT POSITIONING SYSTEM

CROSS-REFERENCE TO RELATED APPLICATIONS

This application claims priority from U.S. Provisional application No. 61/054,214 filed May 19, 2008, the entire subject matter thereof being incorporated herein by reference.

TECHNICAL FIELD

This invention relates generally to automatic patient positioning systems and more particularly to automatic patient positioning systems used in radiological imaging and therapeutic systems having optical scanning for the patient positioning as well as for scan range detection and dynamic patient monitoring during radiographic imaging in such systems.

BACKGROUND

As is known in the art, Computed Tomography (CT) is a tool used for both patient diagnostic examination and to plan modern radiation therapy. Under direction of an radiologists, a CT device generates multiple x-ray images of a patient and assimilates the images into a two-dimensional cross-sectional CT image of the patient's body. Unlike traditional x-ray images, a CT image depicts both hard objects such as bone and soft tissue including tumors. As a result, the CT image may be used for diagnosis, to delineate diseased tissue and healthy organs-at-risk, to define a treatment isocenter, and to design properties of a radiation beam usable to treat the patient (e.g., beam type, shape, dosage, duration).

As is also known in the art, CT virtual simulation gives clinicians the flexibility needed to treat the tumor, while avoiding organs-at-risk. This is done by graphic simulation of the treatment process and designing the optimum scenario for the treatment. The use of CT simulation improves the accuracy of treatment planning. More accurate planning puts a heavy demand on accurate patient positioning. In order to create a CT image, the patient is carefully positioned so as to permit x-ray radiation emitted by the CT device to intercept only an area of the patient's body that is of interest, and to avoid tissue in other areas. Immobilization devices and radiation shields are often used to achieve these ends. Additionally, for acquiring diagnostic CT it is important to minimize the patient preparation time, which includes positioning of the patient on the scanning table depending on various protocols and also acquiring so called topograms to roughly establish the scanning range.

Laser projectors provide one method of marking of the patient. The marks placed on patient skin are then used for the placement of patient under the dose delivery system. Laser making relies on a few points for patient alignment. The alignment of these few points ensures the correct placement of the patient as a whole; however, this technique fails to account for body deformations that often occur during transport of the patient. This problem often occurs during treatment of obese patients, and also for the treatment of the breast. For example, it is important to reposition the patient in such a way that a compliant breast is the exact shape as it was while the patient was on the CT table. Lasers are also used in general scanning to mark the "iso-center" which indicates the region where the physician is interested to scan. The concept of the laser for radiotherapy is bit more precise since the patient position needs to be reproduced at the time of the treatment.

Treatment plans are designed to maximize radiation delivered to a target while minimizing radiation delivered to healthy tissue. However, a treatment plan is designed assuming that relevant portions of a patient will be in a particular position during treatment. If the relevant portions are not positioned exactly as required by the treatment plan, the goals of maximizing target radiation and minimizing healthy tissue radiation may not be achieved. More specifically, errors in positioning the patient can cause the delivery of low radiation doses to tumors and high radiation doses to sensitive healthy tissue. The potential for misdelivery increases with increased positioning errors.

As is also known in the art, Polhemus (Colchester, Vt., USA) currently markets laser based three dimensional (3D) scanning system (an object 3D optical imaging system wherein, for each X-Y position on the object, in additional to data representative of the intensity or reflected energy received by the system at such X,Y position, data is obtained of the distance (i.e., depth) from such position on the object from the focal plane of the system) that is called a FastSCAN system. This system exploits a laser source, single or stereo camera system, plus a magnetic tracking device in order to instantly acquire three dimensional surface images when one sweeps the handheld laser scanning wand over an object. This is done in a manner similar to spray painting. FastSCAN system works by projecting a fan of laser light on the object while the camera views the laser to record cross-sectional depth profiles. Metron Systems Inc. (Snoqualmie, Wash., USA) has similar concept except that the laser and camera systems are mounted on platform which has a controlled translational motion. Most of the 3D optical imaging systems are geared toward industrial applications requiring very high precision for applications such as reverse engineering of parts, rapid prototyping, and/or quality control.

One technique suggested for positioning a region of a subject to be examined is in U.S. Patent Application publication No. 2007/0172102 A1, published Jul. 26, 2007.

SUMMARY

In accordance with the present invention, a patient positioning system is provided for positioning a patient relative to radiographic equipment. The system includes: a 3D optical imaging system for optically scanning the patient, such 3D optical imaging system having a focal plane and providing, for each position on the object, data representative of the intensity of reflected energy received by the system from such position and data representative of distance from such position on the object to the focal plane; a table apparatus for supporting the patient and for moving the table relative to the radiographic equipment in response to positioning signals; and a processor responsive to data from the radiographic equipment and the data from the a 3D optical imaging system for producing the positioning signals.

In one embodiment, the 3D optical imaging system is fixed relative to the radiographic equipment.

In one embodiment, the radiographic equipment is computed tomography equipment.

In one embodiment, the computed tomography equipment has a bore for receiving the table as such table passes from a region external of the bore into the bore, and wherein the 3D optical imaging system has a field of view, such field of extending from the region external of the bore and into a portion internal of the bore.

In one embodiment, the portion of the field of view extends into the bore includes therein a portion of the patient when the patient is positioned in the bore.

In one embodiment, a method is provided for positioning a patient relative to radiographic equipment with a patient positioning system comprising: a 3D optical imaging system for optically scanning the patient, such optical system having a focal plane and providing, for each position on the object, data representative of the intensity of reflected energy received by the system from such position and data representative of distance from such position on the object to the focal plane of the system; a table apparatus for supporting the patient and for moving the table relative to the radiographic equipment in response to positioning signals; a processor responsive to data from the radiographic equipment and the data from the a 3D optical imaging system for producing the positioning signals. The method includes: performing a calibration process to generate coordination transformation between a coordinate system used by the 3D optical imaging system and a coordinate system used by the radiological imaging system, comprising: fixing a phantom on the table; scanning the phantom with the 3D optical imaging system; scanning the phantom with the radiological imaging system; constructing a 3D mesh from the imaging system scan in the coordinate system used by the radiological imaging system; identifying landmarks for both the radiological imaging system scan and the 3D optical image scan; and using a registration process to map the landmarks from the radiological imaging system scan and the 3D optical image scan to generate the coordination transformation between the coordinate system used by the 3D optical image scanning system and the coordinate system used by the radiological imaging system.

In one embodiment, a method is provided for positioning a patient relative to radiographic equipment with a patient positioning system comprising: a 3D optical imaging system for optically scanning the patient, such optical system having a focal plane and providing, for each position on the object, data representative of the intensity of reflected energy received by the system from such position and data representative of distance from such position on the object to the focal plane of the system; a table apparatus for supporting the patient and for moving the table relative to the radiographic equipment in response to positioning signals; a processor responsive to data from the radiographic equipment and the data from the a 3D optical imaging system for producing the positioning signals. The method includes: performing a calibration process to generate a coordination transformation between a coordinate system used by the 3D optical imaging system and a coordinate system used by the radiological imaging system; with the patient on the table, scanning the patient with the 3D optical imaging system to obtaining optical energy intensity data and depth data over a field of view of the 3D optical scanning system; constructing a 3D mesh of the patient from the data obtained with the 3D optical imaging system; identifying a body section of the patient on the constructed mesh to be radiologically scanned; specifying a scan range of the identified section in the coordinate system of the radiographic imaging system based on the specified scan range and the generated coordinate transformation.

In one embodiment, a method is provided for displaying temporal (i.e., time) changes in a patient positioned with a bore of radiographic equipment comprising: a 3D optical imaging system for optically scanning the patient, such optical system having a focal plane and providing, for each position on the object, data representative of the intensity of reflected energy received by the system from such position and data representative of distance from such position on the object to the focal plane of the system; and a table apparatus for supporting the patient. The method includes: performing a calibration process to generate a coordination transformation between a coordinate system used by the 3D optical imaging system and a coordinate system used by the radiological imaging system; with the patient positioned in the bore, continuously scanning the patient in real time with a portion of the field of view extending into the bore with the 3D optical scanning; constructing a 3D mesh of the portion of the patient being optically scanned; identifying temporal changes in the mesh topology; and displaying such temporal changes as a surrogate for patient breathing and/or movement used into the 3D optical image scanning system in the coordinate system used by the radiological imaging system using the generated coordination transformation.

With such arrangements an optical system is provided that is coupled with a radiological imaging such as a Magnetic Resonance Imaging (MRI) or Computed Tomography (CT) machine or a therapeutic system such as a linear accelerator (LINAC). The purpose of the optical system is to scan the patient prior to the radiological scan or the therapeutic procedure in order to first automatically recognize the patient position and second to automatically detect the radiological scan range according to various scanning/imaging protocols. The details of one or more embodiments of the invention are set forth in the accompanying drawings and the description below.

Other features, objects, and advantages of the invention will be apparent from the description and drawings, and from the claims.

DESCRIPTION OF DRAWINGS

FIG. 3 is a flowchart of a process used to calibrate the patient positioning system of FIG. 1;

FIG. 4 is a flowchart of a process used by the patient positioning system of FIG. 1 in providing automatic scan range detection in such system according to the invention;

Like reference symbols in the various drawings indicate like elements.

DETAILED DESCRIPTION

The following description is presented to enable one of ordinary skill in the art to make and use the invention. Descriptions of specific embodiments and applications are provided only as examples and various modifications will be readily apparent to those skilled in the art. The general principles described herein may be applied to other embodiments and applications without departing from the scope of the invention. Thus, the present invention is not to be limited to the embodiments shown, but is to be accorded the widest scope consistent with the principles and features described herein. For purpose of clarity, details relating to technical material that is known in the technical fields related to the invention have not been described in detail.

Figure 1:
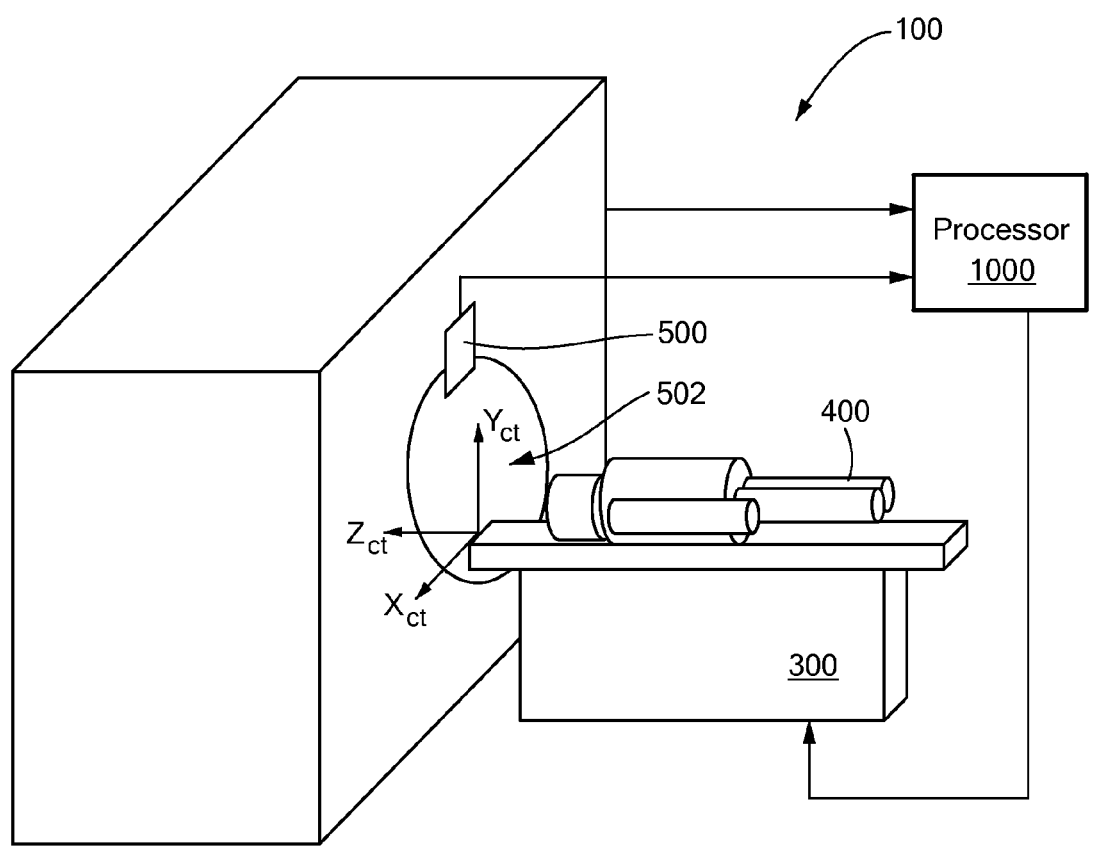
FIG. 1 is a diagram of a patient positioning system for positioning a patient relative to radiographic equipment in accordance with the invention.

Referring now to FIG. 1, a patient positioning system is shown for positioning a patient relative to radiographic equipment, here computed tomography ("CT") equipment. It should be understood that the radiographic equipment may be radiological imaging such as a Magnetic Resonance Imaging (MRI) or Computed Tomography (CT) machine or a therapeutic system such as a linear accelerator (LINAC). The patient positioning system includes a 3D imaging system fixed relative to the computed tomography ("CT") equipment, for optically scanning the patient. The optical system has a focal plane and providing, for each position on the object, data representative of the intensity of reflected energy received by the system at such position and data representative of distance from such position on the object to the focal plane of the system. The patient positioning system includes: a table apparatus for supporting the patient and for moving the table relative to the radiographic equipment in response to positioning signals; and a processor responsive to data from the radiographic equipment and the data from the a 3D imaging system for producing the positioning signals.

More particularly, FIG. 1 shows a computed tomography ("CT") room 100 configured to acquire data in accordance with some embodiments of the present invention. CT room 100 includes CT device 200, CT table 300, patient 400, and 3D optical imaging apparatus 500 mounted to the device 200, as shown. CT device 200 is used to obtain CT data representing at least a portion of patient 400. Specifically, CT device acquires CT data by exploiting the x-ray principal: as x-rays pass through the body they are absorbed or attenuated at differing levels, thereby creating a matrix or profile of x-ray beams of different strength. In conventional x-ray imaging, an image of the profile is produced using film that is sensitive to x-rays. In the case of CT, the film is replaced by a banana-shaped detector that measures the x-ray profile and outputs data representing the profile.

The x-ray detector, not shown, is mounted on a rotating frame inside CT device 200. Mounted opposite to the detector is an x-ray tube that emits a fan beam of x-rays as the rotating frame spins the x-ray tube and detector around patient 400. As the x-ray tube and detector spin, the detector measures profiles of the attenuated x-ray beam. Typically, in one 360 degree spin, about 1,000 profiles are measured. Each profile is subdivided spatially by the detector and fed into about 700 individual data channels. Each profile is then reconstructed into a two-dimensional image of the portion or "slice" that was scanned. The two-dimensional images may be processed to create a three-dimensional image. Both the two-dimensional images and the three-dimensional image are referred to herein as CT data, and both show tissue as well as bone. In some embodiments, the acquired CT data are represented in a CT coordinate frame, depicted by $f_{ct}$: $(x_{ct}, y_{ct}, z_{ct})$ of FIG. 1.

CT table 300 is used to position a patient before, during and after acquisition of CT data. As such, CT table 300 is capable of moving so as to place relevant portions of the patient 400 in the path of the x-ray beam within CT device 200. This movement may be under the control of an operator and/or a computer program. It should be noted that any currently or hereafter-known CT table and CT device may be used in accordance with the present invention.

Figure 2:
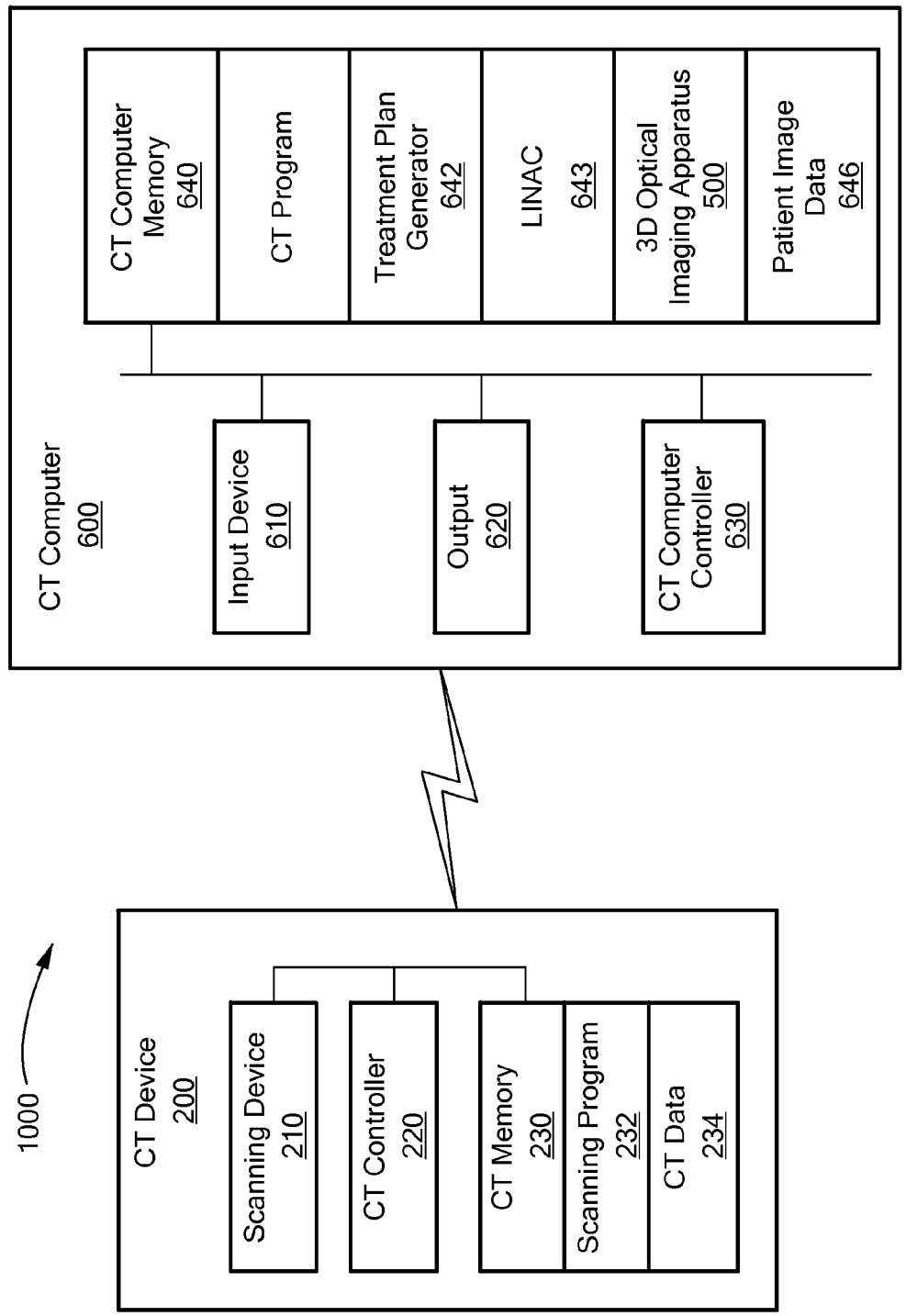
FIG. 2 is a block diagram of equipment used in the patient positioning system of FIG. 1.

FIG. 2 illustrates internal architectures of various elements of CT room 100, including CT device 200 and 3D optical imaging 500. Also illustrated is an internal architecture of CT computer 600, which is not shown in CT room 100. CT computer 600 may be operated so as to cause CT device 200 to perform steps in accordance with embodiments of the present invention. CT computer 600 may be located within CT room 100, in a radiation-proof room adjacent to CT room 100, or elsewhere.

As shown, CT device 200 includes radiographic scanning device 210, which includes the x-ray tube and detector described above as well as other physical devices needed to generate x-ray profiles. CT controller 220 controls scanning device 210 using internal logic and/or executable process steps. Accordingly, scanning device 210 may comprise a microprocessor, a programmable logic controller or the like. Some of these process steps may be part of scanning program 232 stored in memory 230. In this regard, scanning program 232 includes executable process steps for controlling the hardware elements of CT device 100 to scan a body and to thereby generate x-ray profiles. The generated x-ray profiles are stored in memory 230 as CT data 234. CT data 234 may include raw profile data, two-dimensional images generated based on raw profile data, and three-dimensional images generated based on raw profile data and/or two-dimensional images.

CT computer 600 includes input device 610, output device 620, CT computer controller 630, and CT computer memory 640. Input device 610 may be manipulated by an operator to submit commands to CT computer 600 and to CT device 200. Input device 610 may therefore comprise one or more of a keyboard, a pointing device, a touch screen or any other input device. Output device 630 is used to output images, data and text to the operator, and therefore may comprise a display, a printer, and the like. Data may also be input to and output from CT computer 600 using a communication port (not shown) that links CT computer 600 to other devices. For example, commands may be transmitted to and CT data may be received from CT device 200 over such a communication port.

CT computer controller 630 controls elements of CT computer 600 according to internal logic and/or executable process steps. The process steps may be received from another device or stored in memory 640. Process steps used to control the functions of CT device 200 are found in CT program 641. Treatment plan generator stores process steps that are executable to generate a radiation treatment plan based on CT data, virtual camera images, and data of for a linear accelerator (linac) 643, not shown.

CT computer data 644 includes CT data 234 generated by CT device 200 in any format, including raw and/or image format. The 3D imaging optical apparatus 500 creates a 3D image (i.e., optimal intensity and depth, as described above) data 646 that is in the coordinate system of the 3D optical imaging apparatus 500. A calibration procedure described below generates coordinate transformation terms relating the coordinate system of the CT apparatus 200 and the 3D optical imaging system 500.

Each of the devices shown in FIG. 2 may include less or more elements than those shown. In addition, embodiments of the invention are not limited to the two devices shown.

Briefly, in accordance with the invention, 3D optical scanning of a body is extended to applications within medical imaging arena. Specifically, the system described in more detail below, automatically recognizes the patient position on the imaging couch (i.e., table) of CT scanning apparatus as shown in FIG. 1. The system, to be described, also detects various anatomical sections required for different radiological scanning protocols. Here, two preferred embodiments are described. The first embodiment uses for the 3D scanning system 500, a 3D time of flight (TOF) camera such as (Mesa Imaging AG, Zuerich, Switzerland) is used within or close to the CT scanner bore. The main purpose of this camera is to acquire the 3D optical profile of the patient while the patient is automatically transferred (using the imaging system couch inside of the bore prior to radiological scanning process. Since the field of view of the camera is limited, both depth and optical images of the patient need to be stitched together to get a full whole body optical scan of the patient. The whole body surface mesh of the patient is extracted from the whole body stitched depth image. This whole body compounded optical image and the surface mesh of the patient from the 3D TOF camera plus and an additional optical image from a side camera are then processed to extract the patient position (e.g., Head First Supine . . . ) and anatomical based radiological scan ranges.

In the second embodiment, a combination of a line projector (laser or collimated line strip) and a camera is used for the 3D optical scanning system 500. The projected light encodes the patient profile (relative to the couch) as seen on the sequence of optical images as the patient is transported into the scanner by the imaging couch 300. These profiles at each couch position are then stitched together to provide a three-dimensional whole body surface mesh of the patient.

Calibration

In both embodiments the reconstructed 3D optical surface mesh points need to be transformed into the radiological scanner or the therapeutic machine coordinate system (e.g., CT imaging coordinate system). As the optical imaging system 500 is mechanically attached to the frame of the radiological scanning system 200, this relationship can be thought to be constant and needs to be calibrated once. However, in order to be able to accurately stitch and combine the 3D reconstruction, accurate (repeatable) couch position information needs to be exploited as well.

In order to do such a calibration, a phantom is used with specific set of landmarks, which can be uniquely identified in both reconstructed radiological volume and optically extracted surface mesh.

The calibration process can be outlined as follows:

Scan the phantom using the 3D optical imaging system 500 and record information such as couch position in millimeters and the optical images at each couch position.

Reconstruct a surface mesh using the optical images.

Scan the phantom using radiological imaging system and reconstruct the image in the (global) radiographic imaging coordinate system (NOT the patient optical coordinate system).

Identify a set of corresponding landmarks between the two reconstructions.

Use the landmarks to find a homogenous transformation mapping these coordinate systems to one another.

More particularly, referring to FIG. 3, the phantom is fixed on the CT couch 300, Step 302. Next, the phantom is scanned using the 3D optical scanning system 500, Step 304. Next, a 3D mesh is constructed using data from the optical scans, Step 306. Next, the fixed phantom is scanned using radiological imaging system 200, Step 308. Next, a set of corresponding landmarks is identified from both the radiologically scan and the optical scan, Step 310. Next, a registration process is used to map the landmarks from the data from the optical scans to the data radiologically scanned and thereby generate a coordination transformation between a coordinate system used by the optical system 500 and a coordinate system used by the radiological imaging apparatus 200, Step 312.

Automatic Scan Range Detection

Referring now to FIG. 4, the process for automatic scan range detection is shown. The process is used for positioning the patient relative to the radiographic equipment. As noted above, the patient positioning system includes the 3D optical imaging system 500 (FIG. 1) for optically scanning the patient 400. The optical system 500 has a focal plane (not shown) and provides, for each position on the patient 400, data representative of the intensity of reflected energy received by the system from such position and data representative of distance from such position on the patient 400 to the focal plane of the system; a table apparatus 300 for supporting the patient 400 and for moving the table 300 relative to the radiographic equipment 200 in response to positioning signals; a processor 1000 responsive to data from the radiographic equipment 200 and the data from the a 3D optical imaging system 500 for producing the positioning signals for the table apparatus 300. The method of positioning the table apparatus 300 includes performing the calibration procedure described above in connection with FIG. 3. Thus, the method first performs the calibration to generate coordination transformation between a coordinate system used by the 3D optical imaging system 500 and a coordinate system used by the radiological imaging system 200.

With the patient 400 on the table 300, (Step 402) the process scans the patient 400 with the 3D optical imaging system 200 to obtaining optical energy intensity data and depth data over a field of view of the 3D optical scanning system 200, Step 404. Next, the optical intensity and depth images are stitched for various couch positions as the patient is moved into the bore 502, Step 406. Next, the processor 1000 constructs a "whole body" 3D mesh of the patient along with the corresponding optical image, Step 408. The "whole body" mesh is used to identify various body section either using atlases or landmark detection techniques, Step 410. (As described in more detail below, see "Atlas-Based Recognition of Anatomical Structures and Landmarks to Support the Virtual Three-Dimensional Planning of Hip Operations", Medical Image Computing and Computer-Assisted Intervention—MICCAI 2003. Furthermore for the optical images, an outline of the patient is extracted a knowledge based technique is used as described in Bottom-up Recognition and Parsing of the Human Body, IEEE Conference on Computer Vision and Pattern Recognition (CVPR), 2007.)

Next, the radiologist specifies a scan range in the coordinate system of the imaging device based on the specified range and the coordinate transformation terms obtained during the calibration process, Step 412. The range information is used to generate the position signal for the table 300.

Stitching Issues (Image Processing As the couch 300 transports the patient into the imaging bore 502, a sequence of optical (i.e., optical intensity) and depth images are acquired by the 3D optical imaging system 500. The first issue is how to stitch these optical images in order to have a seamless compounded whole body optical intensity and depth image (i.e., 3D optical image) of the patient, which can be processed and displayed in lieu of, for example, topograms in computer tomography (CT). Further, it can be used to reconstruct whole body surface mesh of the patient. In order to do this, only small area of the images is used, which is passing though the middle section of the image and is perpendicular to the direction of the couch movement. This selection is mainly made to minimize the inaccuracies that might arise from stitching of the overlapping consecutive perspective images.

Scan Range Detection Issues (Recognition)

Once the whole body optical (i.e., optical intensity) and/or depth compounded 3D optical image is constructed the second step is to recognize various sections of this (these) optical image(s) or the surface mesh corresponding to specific optical anatomical landmarks. Here, an atlas based approach is used to deal with the reconstructed optical surface mesh of patient using the depth information, as is described in Atlas-Based Recognition of Anatomical Structures and Landmarks to Support the Virtual Three-Dimensional Planning of Hip Operations, Medical Image Computing and Computer-Assisted Intervention—MICCAI 2003. Furthermore for the optical images, an outline of the patient is extracted a knowledge based technique is used as described in Bottom-up Recognition and Parsing of the Human Body, IEEE Conference on Computer Vision and Pattern Recognition (CVPR), 2007.

Auto Centering the Imaging Couch

In additional to scanning range detection, the optically generated surface mesh, along with the stitched optical images (from top and the side) can be used to estimate the position of the internal organs based on a-priori knowledge of anatomy derived from a model patient CT scan. This information can be used within some of the scanning protocols, where it is required to change the height of the imaging couch automatically in order to focus on a volume of interest (VOI) (e.g., head or kidneys).

Dynamic Patient Monitoring

Figure 7:
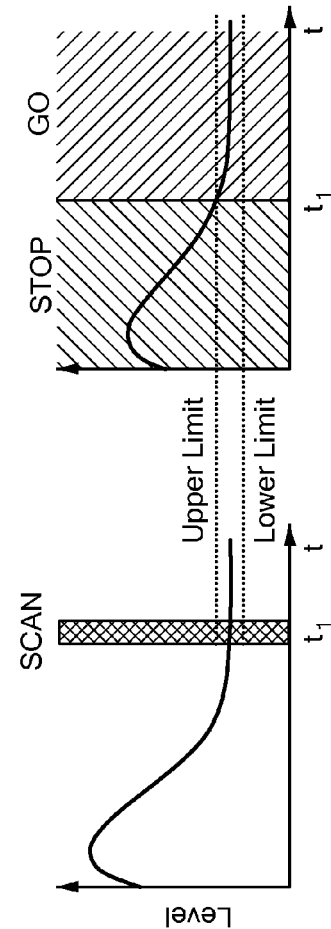
FIG. 7 shows on the left dynamic patient monitoring based a motion surrogate (left) in order to generate indication for either image gating or an interventional action (stop and go linac procedure, for example, depicted in the right image) in accordance with the automatic patient motion detection process of FIGS. 5 and 6.

Both embodiments can be used in the dynamic mode. The real time surface measurements from the first embodiment can be used as a surrogate for patient movement in real-time. The real-time surface encodes both patient physical movements and also physiological changes and movements, for instance, due to the breathing. Surface measurements (point cloud) generated in (near) real-time need to be processed and the measurement dimension needs to be reduced to, for instance, one as shown in FIG. 7. The dimension reduction methods such as the one described in [Ali Khamene, Jan K. Warzelhan, Sebastian Vogt, Daniel Elgort, Christophe Chefd'Hotel, Jeffrey L. Duerk, Jonathan S. Lewin, Frank K. Wacker, Frank Sauer: Characterization of Internal Organ Motion Using Skin Marker Positions. MICCAI (2) 2004: 526-533 can be used. One possible solution is, for example, the geodesic length between one corresponding point pair across the time varying surface measurements. The length resembles the strain measured by a belt as implemented in commercial breathing surrogate devices such as ANZAI [ANZAI MEDICAL CO., LTD 3-6-25 Nishi-shinagawa Shinagawa-ku, Tokyo 141-0033, Japan].

In the second embodiment, the real-time depth profile of the patient reconstructed based on the projection of single or double line laser(s) or collimated light strip(s) can be used as a breathing surrogate. The dimension reduction in this case is simpler since the signal is already spatially one dimensional.

The estimated real-time respiratory state of the patient can be used to:

Support CT interventions, where in a stop and go manner the system can show, the interventional radiologist, the time interval at which the actual respiratory state is matching the patient physiological state (e.g., breathing) imaged and used for guidance. FIG. 7) shows on the left dynamic patient monitoring based a motion surrogate (left) in order to generate indication for either image gating or an interventional action (LINAC gating procedure, for example, depicted in the right image) in accordance with the invention.

During the gating procedure the radiation beam is turned on and off depending on the amplitude of the surrogate signal (i.e., the signal generated from the patient in real-time as (s)he/she breathes. More particularly, the signal extracted from the moving mesh (such moving resulting from results of scanning patient while breathing and which is representative of the patient's breathing pattern.

The specific amplitude of the surrogate signal is recorded during the planning as the indication of the patient physiological state. During the treatment the beam is turned on only if the real-time surrogate signal amplitude is within a range of the planned amplitude, otherwise the beam is off. The procedure ensures that the radiation is only applied to the tumor at the planned position.

Use it as a bio-feedback for the patient in order to reproduce a specified respiratory state (coached breathing), Combine with an navigation system to support respiratory correction and compensation (for example using 4D CT), Use it as a part of the radiotherapy planning procedure and to compare the follow-up scans, Finally, use it to bin and retro-respectively reconstruct multiple phases of CT scans (gated reconstruction).

Figure 6:
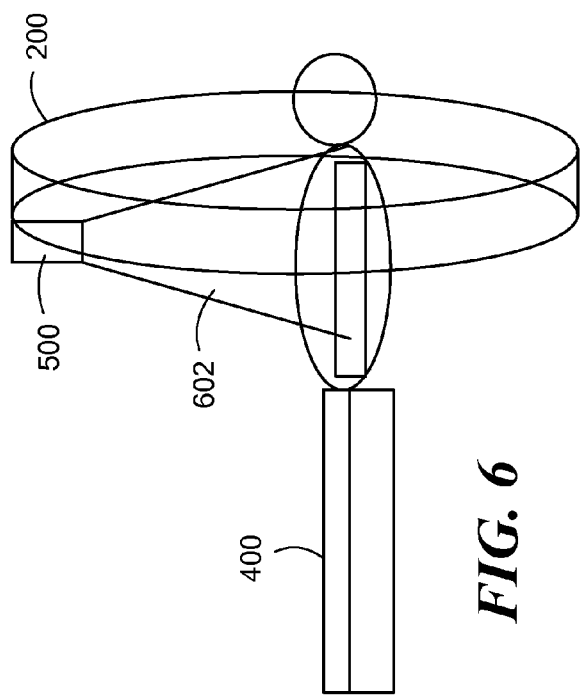
FIG. 6 is a diagram of the patient positioning system of FIG. 1 showing a filed of view of a 3D imaging system used in such system and used in the automatic patient motion detection process of FIG. 6.
Figure 5:
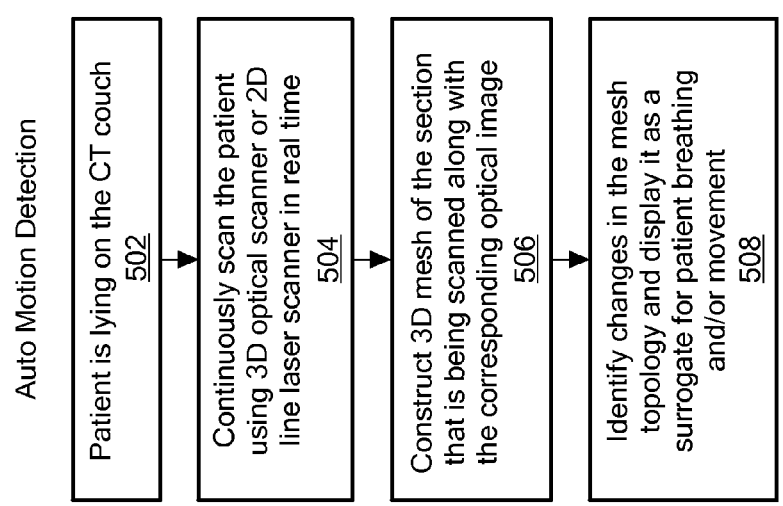
FIG. 5 is a flowchart of a process used by the patient positioning system of FIG. 1 in providing automatic patient motion detection in such system according to the invention.

More particularly, and referring to FIG. 5, with the patient lying on the CT couch, Step 502, the patient is continuously scanned using 3D optical scanning system 500 in real time, Step 504. It is noted from FIG. 6 that a portion of the field of view 602 of the optical system 500 extends into the frontal portion of the bore onto a portion of the patient. Next, the processor 1000 constructs a 3D mesh of the section that is being radiologically scanned along with the corresponding optical image, Step 506. Next, the processor 1000 identifies changes in the mesh topology and displays such changes as a Surrogate for patient breathing and/or movement, Step 508.

Additional Aspects

The generated surface especially in the area of the face can be used for verifying patient identification, specifically for the follow-up scans. On demand optical rescanning of the patient can also reveal patient movements during an interventional or therapeutic procedure.

Variations and Extensions

The invention can be extended to just use compounded optical images without the depth image or the reconstructed surface mesh. For these cases, the optical images need to be processed robustly enough for the purpose of body section detection. Dynamic (temporal) changes within the optical images can also be quantified as used a surrogate for motion. The optical scanning system (both embodiments) can be used in conjunction with a therapeutic system such as linear accelerator. If the therapeutic system has an on-board imaging capability, the calibration method as explained can directly be applied. Otherwise, a mechanical calibration method should be utilized. Furthermore, other 3D scanning technologies can interchangeably be used as long as the calibration procedure is performed as explained above.

A number of embodiments of the invention have been described. Nevertheless, it will be understood that various modifications may be made without departing from the spirit and scope of the invention. Accordingly, other embodiments are within the scope of the following claims.

What is claimed is:

1. A patient positioning system for positioning a patient relative to radiographic equipment, such system comprising:
 a 3D optical imaging system for optically scanning the patient, such 3D optical imaging system having a focal plane and providing, for each position on the object, data representative of the intensity of reflected energy received by the system from such position and data representative of distance from such position on the object to the focal plane;

a table apparatus for supporting the patient and for moving the table relative to the radiographic equipment in response to positioning signals;

a processor responsive to data from the radiographic equipment and the data from the 3D optical imaging system for producing the positioning signals; and wherein the line projector is a collimated line strip.

2. The system recited in claim 1 wherein the radiographic equipment is computed tomography equipment.

3. A patient positioning system for positioning a patient relative to radiographic equipment, such system comprising:

a 3D optical imaging system for optically scanning the patient, such 3D optical imaging system having a focal plane and providing, for each position on the object, data representative of the intensity of reflected energy received by the system from such position and data representative of distance from such position on the object to the focal plane;

a table apparatus for supporting the patient and for moving the table relative to the radiographic equipment in response to positioning signals;

a processor responsive to data from the radiographic equipment and the data from the 3D optical imaging system for producing the positioning signals;

wherein the radiographic equipment is computed tomography equipment; and wherein the computed tomography equipment has a bore for receiving the table as such table passes from a region external of the bore into the bore, and wherein the 3D optical imaging system has a field of view, such field of extending from the region external of the bore and into a portion internal of the bore.

4. The system recited in claim 3 wherein the 3D optical imaging system is fixed relative to the radiographic equipment.

5. The system recited in claim 4 wherein the portion of the field of view extending into the bore includes therein a portion of the patient when the patient is positioned in the bore.

6. The system recited in claim 5 wherein the 3D optical imaging system is fixed relative to the radiographic equipment.

7. A method for positioning a patient relative to radiographic equipment with a patient positioning system comprising: a 3D optical imaging system for optically scanning the patient, such optical system having a focal plane and providing, for each position on the object, data representative of the intensity of reflected energy received by the system from such position and data representative of distance from such position on the object to the focal plane of the system; a table apparatus for supporting the patient and for moving the table relative to the radiographic equipment in response to positioning signals; a processor responsive to data from the radiographic equipment and the data from the a 3D optical imaging system for producing the positioning signals, such method comprising:

performing a calibration process to generate coordination transformation between a coordinate system used by the 3D optical imaging system and a coordinate system used by the radiological imaging system, comprising:

fixing a phantom on the table;

scanning the phantom with the 3D optical imaging system;

scanning the phantom with the radiological imaging system;

constructing a 3D mesh from the imaging system scan in the coordinate system used by the radiological imaging system;

identifying landmarks for both the radiological imaging system scan and the 3D optical image scan;

using a registration process to map the landmarks from the radiological imaging system scan and the 3D optical image scan to generate the coordination transformation between the coordinate system used by the 3D optical image scanning system and the coordinate system used by the radiological imaging system.

8. A method for positioning a patient relative to radiographic equipment with a patient positioning system comprising: a 3D optical imaging system for optically scanning the patient, such optical system having a focal plane and providing, for each position on the object, data representative of the intensity of reflected energy received by the system from such position and data representative of distance from such position on the object to the focal plane of the system; a table apparatus for supporting the patient and for moving the table relative to the radiographic equipment in response to positioning signals; a processor responsive to data from the radiographic equipment and the data from the a 3D optical imaging system for producing the positioning signals, such method comprising:

performing a calibration process to generate a coordination transformation between a coordinate system used by the 3D optical imaging system and a coordinate system used by the radiological imaging system;

with the patient on the table, scanning the patient with the 3D optical imaging system to obtaining optical energy intensity data and depth data over a field of view of the 3D optical scanning system;

constructing a 3D mesh of the patient from the data obtained with the 3D optical imaging system;

identifying a body section of the patient on the constructed mesh to be radiologically scanned;

specifying a scan range of the identified section in the coordinate system of the radiographic imaging system based on the specified scan range and the generated coordinate transformation.

9. The method recited in claim 8 wherein the calibration comprises:

fixing a phantom on the table;

scanning the phantom with the 3D optical imaging system;

scanning the phantom with the radiological imaging system;

constructing a 3D mesh from the imaging system scan in the coordinate system used by the radiological imaging system;

identifying landmarks for both the radiological imaging system scan and the 3D optical image scan;

using a registration process to map the landmarks from the radiological imaging system scan and the 3D optical image scan to generate the coordination transfoimation between the coordinate system used by the 3D optical image scanning system and the coordinate system used by the radiological imaging system.

10. A method for displaying temporal changes in a patient positioned within the bore of radiographic equipment comprising: a 3D optical imaging system for optically scanning the patient, such optical system having a focal plane and providing, for each position on the object, data representative of the intensity of reflected energy received by the system from such position and data representative of distance from such position on the object to the focal plane of the system; and a table apparatus for supporting the patient, such method comprising:

performing a calibration process to generate a coordination transformation between a coordinate system used by the 3D optical imaging system and a coordinate system used by the radiological imaging system;

with the patient positioned in the bore, continuously scanning the patient in real time with a portion of the field of view extending into the bore with the 3D optical scanning;

constructing a 3D mesh of the portion of the patient being optically scanned;

identifying temporal changes in the mesh topology; and displaying such temporal changes as a surrogate for patient breathing and/or movement used into the 3D optical image scanning system in the coordinate system used by the radiological imaging system using the generated coordination transformation.

11. The method recited in claim 10 wherein the calibration comprises:

fixing a phantom on the table;

scanning the phantom with the 3D optical imaging system;

scanning the phantom with the radiological imaging system;

constructing a 3D mesh from the imaging system scan in the coordinate system used by the radiological imaging system;

identifying landmarks for both the radiological imaging system scan and the 3D optical image scan;

using a registration process to map the landmarks from the radiological imaging system scan and the 3D optical image scan to generate the coordination transformation between the coordinate system used by the 3D optical image scanning system and the coordinate system used by the radiological imaging system.

12. A patient positioning system for positioning a patient relative to radiographic equipment, such system comprising:

a 3D optical imaging system for optically scanning the patient, such 3D optical imaging system having a focal plane and providing, for each position on the object, data representative of the intensity of reflected energy received by the system from such position and data representative of distance from such position on the object to the focal plane;

a table apparatus for supporting the patient and for moving the table relative to the radiographic equipment in response to positioning signals;

a processor responsive to data from the radiographic equipment and the data from the 3D optical imaging system for producing the positioning signals;

wherein radiographic equipment has a bore for receiving the table as such table passes from a region external of the bore into the bore, and wherein the 3D optical imaging system has a field of view, such field of extending from the region external of the bore and into a portion internal of the bore.

* * * * *